United States Patent [19]
Tamura et al.

[11] Patent Number: 5,353,791
[45] Date of Patent: Oct. 11, 1994

[54] OPTICAL ORGANISM MEASURING APPARATUS

[75] Inventors: Tomomi Tamura; Hideo Eda, both of Kyoto, Japan

[73] Assignee: Shimadzu Corporation, Kyoto, Japan

[21] Appl. No.: 838,848

[22] Filed: Feb. 21, 1992

[30] Foreign Application Priority Data

Feb. 28, 1991 [JP] Japan ................................. 3-17688

[51] Int. Cl.⁵ ................................................ A61B 5/00
[52] U.S. Cl. ................................... 128/633; 128/664; 128/665; 356/41
[58] Field of Search ........ 128/633, 664, 665, 666–667, 128/634; 351/221; 356/39–41

[56] References Cited

U.S. PATENT DOCUMENTS

| | | |
|---|---|---|
| 4,321,930 | 3/1982 | Jobsis et al. ..................... 128/633 |
| 4,704,029 | 11/1987 | Van Hevelen ..................... 356/39 |
| 5,137,023 | 8/1992 | Mendelson et al. ............... 128/633 |

*Primary Examiner*—Angela D. Sykes
*Attorney, Agent, or Firm*—William L. Klima

[57] ABSTRACT

Disclosed herein is an optical organism measuring apparatus in which cables provided on both light transmission and receiving sides are sufficiently reduced in diameter and provided with flexibility for attaining handleability while light can be transmitted and received in high efficiency so that information can be obtained from a deep portion in an organism. Semiconductor lasers (2-1, 2-2, 2-3) are coupled with incident ends of a plurality of single core optical fibers which are contained in a flexible probe (12), so that laser light guided by the single core optical fibers is applied to an organism (8) from a forward end portion of the probe (12). A light receiving probe (18) is provided on its forward end with a silicon photodiode (14), which is attached in close contact to the organism (8) to receive light transmitted through or reflected by the organism (8). This silicon photodiode (14) is integrated with a preamplifier (16). A cable for transmitting a detection signal which is amplified by the preamplifier (16) is formed by a flexible shielding wire.

8 Claims, 4 Drawing Sheets

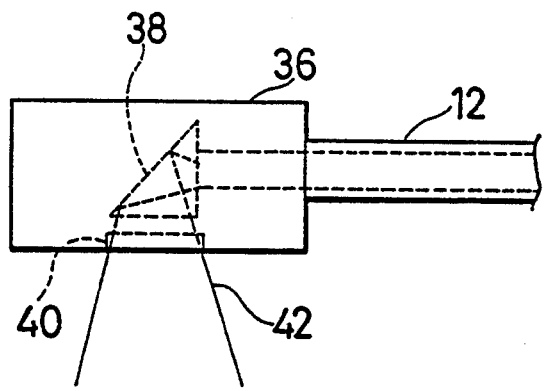
FIG. 2A
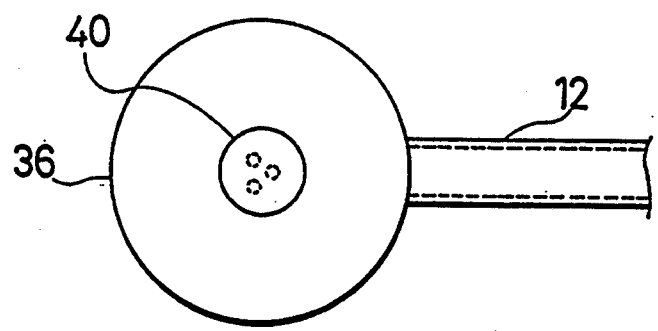
FIG. 2B
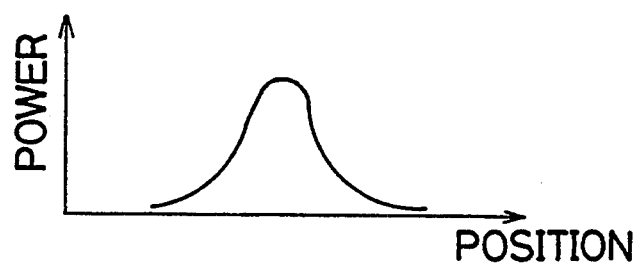
FIG. 2C
FIG. 3
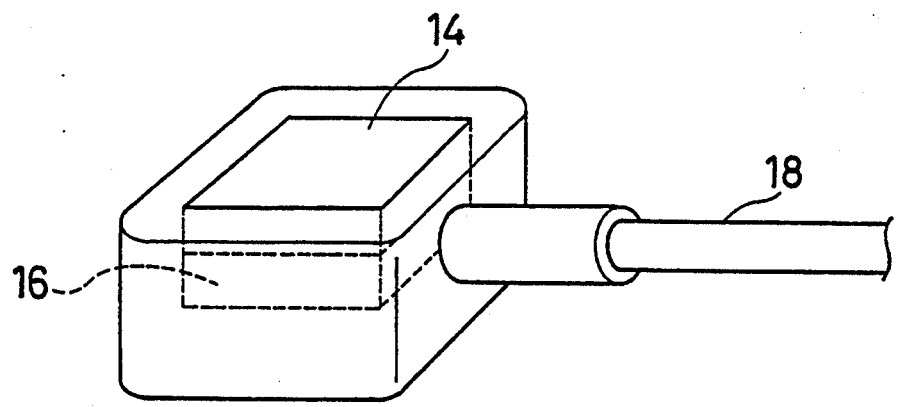

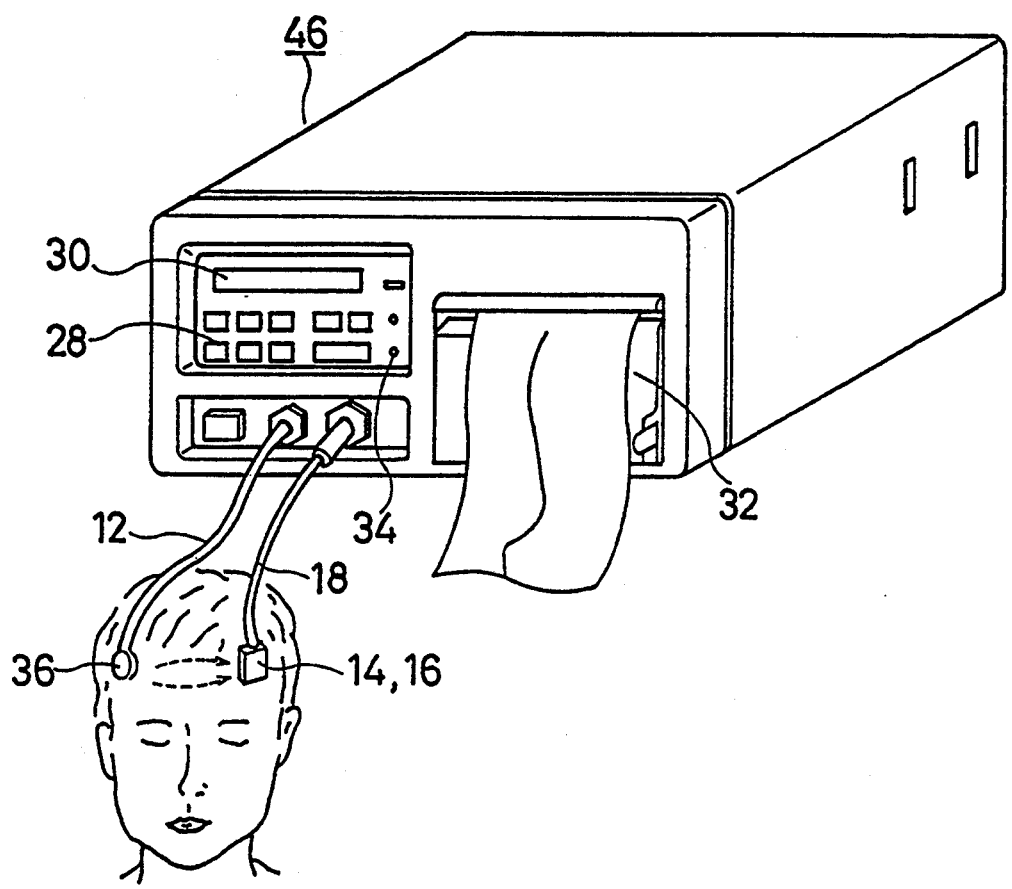

OPTICAL ORGANISM MEASURING APPARATUS

BACKGROUND OF THE INVENTION

1. Field of the Invention

The present invention relates to an optical organism measuring apparatus, which is adapted to obtain vital information by applying light such as visible radiation or near infrared radiation to an organism and measuring the light transmitted through or reflected (including scattered light) by the same.

2. Description of the Background Art

Some of optical measuring apparatuses are provided with optical paths which are formed by optical fibers. For example, a laser tissue blood flow meter, which applies laser light to an organism through a single-core fiber and receives the reflected light by an optical fiber for calculating the tissue blood flow volume, has already been put on the market. The light reflected by the organism is obtained from a portion which is in close proximity to an end exposed to the light.

U.S. Pat. Nos. 4,223,680 and 4,281,645 disclose an apparatus which applies light emitted from a light source to a vital tissue through an optical fiber bundle and receives the light reflected by the vital tissue through a light receiving optical fiber bundle which is arranged on the central axis of the said optical fiber bundle for application of light or another portion for guiding the reflected light to a detector.

There has also been provided an apparatus called a pulse oxymeter, which is adapted to directly fix an LED to an organism and receive light transmitted through a fingertip or the like by a photodiode, thereby measuring oxygen saturation in arterial blood.

Light which is applied for measuring information in an organism is extremely attenuated due to scattering or absorption caused in vivo. Even if narrow light is applied, the same is scattered in the organism and spread over a wide area toward all directions of a $2\pi$ space (half plane) in the detecting side. Therefore, both light transmission and receiving sides must be devised in order to improve sensitivity.

The aforementioned organism measuring apparatus for calculating the tissue blood flow volume has strong intensity for obtaining vital information from a portion in close proximity to an end which is exposed to light by a reflection method, and no problem is caused in particular in a measuring system employing an optical fiber. In order to obtain information from a deep portion in the organism, however, optical fiber bundles which are formed by numbers of optical fibers are generally employed in both light transmission and receiving sides due to strong scattering and absorption caused in vivo. Also in this case, the optical fiber bundle employed in the light receiving side must be increased in thickness if a light transmission length in vivo is about several cm, in order to improve detection sensitivity for light which is transmitted through or reflected by the organism. When the optical fiber bundle is thus increased in diameter, however, it is difficult to stably fix the same to the organism due to its own weight.

Even if the light is received by an optical fiber bundle having a large diameter, there remains a problem of fiber loss which is varied with the charging rate of the optical fibers contained in the optical fiber bundle, the core ratios in the respective optical fibers, the propagation rates of the transmitted or reflected light entering the cores, and the like.

The light receiving side is preferably pressed in close contact against the organism, in order to omnidirectionally catch the transmitted or scattered light over a wide area. In this point, the quantity of light is reduced in relation to a handleable optical fiber bundle having a small diameter, and only light energy within a propagation angle of a core portion of the optical fiber bundle is used.

As to the light transmission side, on the other hand, it is advantageous that a high output can be obtained with monochromatic light. However, in a measuring system such as a pulse oxymeter employing an LED, for example, the as-obtained light output is restricted. Such a pulse oxymeter can merely measure light which is transmitted through a fingerpoint at the most, due to a small light output of the LED. Further, measuring accuracy is deteriorated since the bandwidth of the LED is too large.

SUMMARY OF THE INVENTION

An object of the present invention is to provide a handleable optical organism measuring apparatus comprising a measuring system having light transmission and receiving sides provided with sufficiently thin and flexible cables, which can transmit and receive light with high efficiency to be effectively applied to a method of deeply introducing light into an organism with a light transmission length of several cm.

In order to attain the aforementioned object of the present invention, a light source provided in the light transmission side is formed by a semiconductor laser and light which is emitted from the semiconductor laser is guided to an organism through a single core optical fiber, while the light receiving side is provided with a solid state detector such as a silicon photodiode capable of obtaining a wide area, which is integrated with a preamplifier.

The transmission side can be sufficiently flexible, handleable and lightweight even if optical fibers are bundled in response to a plurality of wavelengths, since the optical fiber are prepared from single core ones. In the light receiving side, on the other hand, a cable from the detector can be reduced in diameter since the preamplifier is integrated with the solid state detector. Thus, the inventive measuring apparatus can be easily fixed to an organism since both the light transmission and receiving sides can be reduced in thickness as well as weight.

Since the light source provided in the light transmission side is formed by a semiconductor laser, measuring light can be brought into a narrow beam, to efficiently transmit strong light with single core optical fibers.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 2(A) is a side elevational view showing an exemplary light transmission probe, FIG. 2(B) is a bottom plan view thereof, and FIG. 2(C) is a graph showing power distribution of laser light as applied;

FIG. 3 is a perspective view showing a light receiving probe;

FIG. 4 is a perspective view showing the appearance of the embodiment; and

DESCRIPTION OF THE PREFERRED EMBODIMENT

Figure 1:
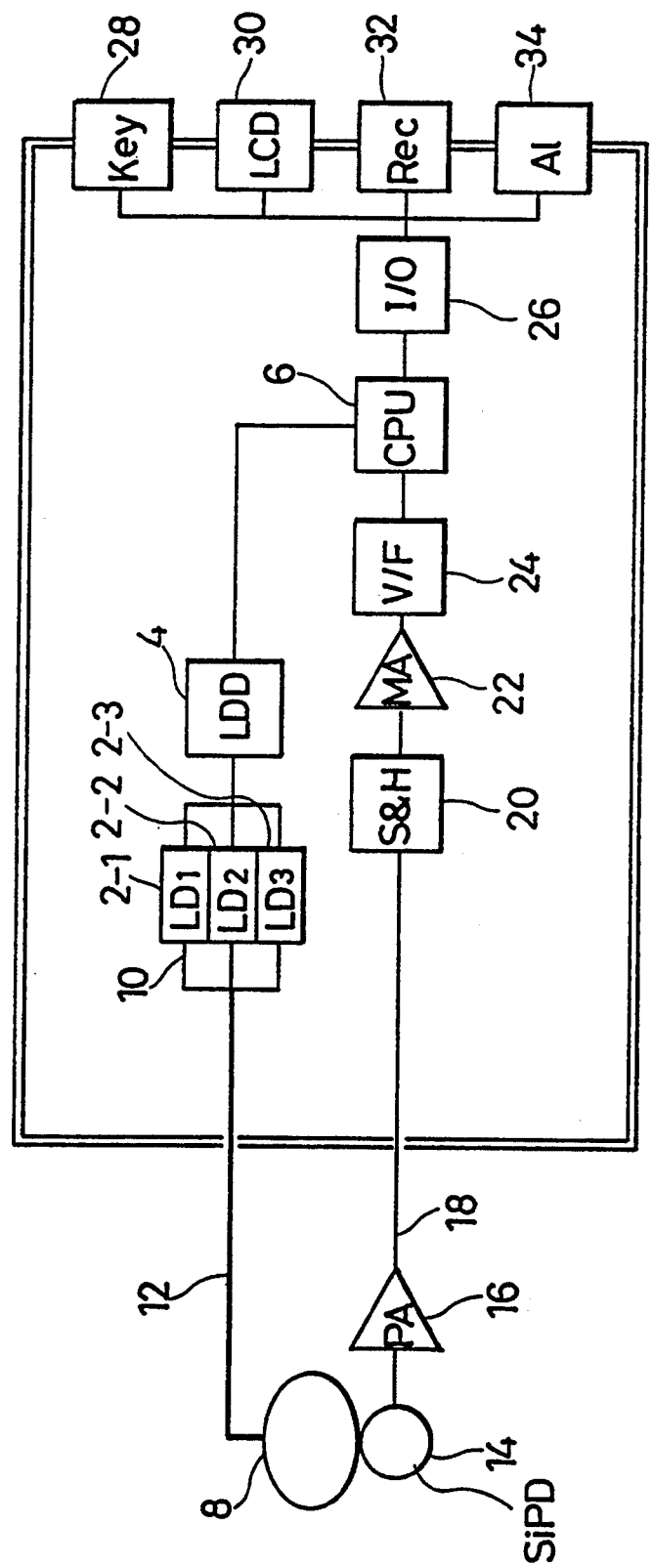
FIG. 1 is a block diagram showing an embodiment of the present invention.

FIG. 1 is a block diagram showing an embodiment of the present invention, which is applied to a near infrared oxygen monitor.

The apparatus shown in FIG. 1 comprises three semiconductor lasers 2-1 to 2-3 of different wavevlengths for calculating three wavelength absorbance values. The semiconductor lasers 2-1 to 2-3 are coupled with incident ends of three single core optical fibers which are contained in a light transmission probe 12 through laser modules (corresponding to FC connectors) 10. The three single core optical fibers, which are branched in the apparatus body, are bundled into a sheath within the probe 12. The probe 12 is flexible with the sheath of about 3 mm in outer diameter. Laser light which is guided by the single core optical fibers is applied from the forward end portion of the probe 12 to an organism 8.

The semiconductor lasers 2-1 to 2-3 oscillate laser beams of specific wavelengths λ1, λ2 and λ3 respectively. The respective outputs are 30 mW, for example. The oscillation wavelengths λ1, λ2 and λ3 are preferably set to be at least 700 nm in combinations of 780 nm, 805 nm and 830 nm or 700 nm, 730 nm and 750 nm, for example, while the same are not restricted to these values but can be set in an arbitrary combination. The semiconductor lasers 2-1 to 2-3 are successively switched for oscillation by a driving circuit 4, which is controlled by a CPU 6.

A light receiving probe 18 is provided on its forward end with a solid state detector of a silicon photodiode 14, which is fixed in close contact to the organism 8, to receive light transmitted through or reflected by the organism 8. The silicon photodiode 14 is integrated with a preamplifier 16. A cable for transmitting a detection signal which is amplified by the preamplifier 16 is made of a flexible shielding wire.

A sample-and-hold circuit 20 is adapted to sample and hold the signal which is amplified by the preamplifier 16, and a main amplifier 22 is adapted to amplify the output signal from the sample-and-hold circuit 20, while a V-F converter 24 is adapted to convert the amplified signal voltage to a frequency. The output signal from the V-F converter 24 is inputted in the CPU 6 and counted.

The CPU 6 controls oscillation of the semiconductor lasers 2-1 to 2-3, and incorporates data at the respective wavelengths λ1, λ2 and λ3, to calculate agebased absorbance changes ΔA1, ΔA2 and ΔA3. The CPU 6 then calculates oxyhemoglobin fluctuation volumes Δ[HbO2] and total hemoglobin fluctuation volumes Δ[THb] from the calculated age-based absorbance changes ΔA1, ΔA2 and ΔA3 and oxyhemoglobin absorbance coefficients k1, k2 and k3 and deoxyhemoglobin absorbance coefficients k1', k2' and k3' which have previously been measured and set, and further calculates oxygen saturation values SO2=Δ[HbO2]/Δ[THb]×100 (%). A method of calculating such hemoglobin volumes has already been proposed by Tamura, one of the inventors (see Japanese Patent Laying-Open Gazette No. 2-95262 (1990)).

$$\Delta[HbO2] =$$

$$\{(k2' - k3')\Delta A1 - (k1' - k3')\Delta A2 + (k1' - k2')\Delta A3\}/K$$

$$\Delta[THb] = \{(k2' - k3' - k2 + k3)\Delta A1 +$$

$$(k1 - k3 - k1' + k3')\Delta A2 + (k1' - k2' - k1 + k2)\Delta A3\}/K$$

$$K = (k1 - k3)(k2' - k3') - (k2 - k3)(k1' - k3')$$

The CPU 6 is connected with a keyboard 28 for operating this apparatus and inputting absorbance coefficients, a liquid crystal display 30 for displaying measured values and the like, a recorder 32 for outputting the results of measurement, an alarm device 34 for information of an abnormal state and the like through an input/output part 26. Referring to FIG. 1, the apparatus body is enclosed by double lines.

Signals detected by the silicon photodiode 14 are operated by the CPU 6, so that the calculated hemoglobin volumes are continuously outputted to the recorder 32, the liquid crystal display 30 and the like.

FIG. 2(A) is a side elevational view showing an exemplary forward end portion 36 of the light transmission probe 12, i.e., a portion to be in contact with the organism 8, FIG. 2(B) is a bottom plan view thereof, and FIG. 3(C) is a graph showing power distribution of the laser light as applied.

A prism is integrated in the forward end portion 36 of the probe 12, so that the laser light can be applied perpendicularly to the direction of the optical fiber axes within the probe 12. A window plate 40 is brought into contact with the organism 8, to drop the laser light which is bent through the prism 38 and apply the same to the organism 8. Since the laser light is perpendicularly bent through the prism 38, it is possible to stick and fix the probe 12 to the organism 8.

FIG. 3 shows an exemplary structure of the light receiving probe 18. The silicon photodiode 14 is adapted to receive the measuring light which is applied to the organism 8 and outputted toward the light receiving side through scattering and absorption within the organism 8. The preamplifier 16 is integrated with the silicon photodiode 14 in order to amplify a detection signal from the silicon photodiode 14 and transmit the same to the apparatus body in a state containing small noise. The signal which is detected by the silicon photodiode 14 is converted from a current to a voltage by the preamplifier 16, and then transmitted to the apparatus body through a thin shielding wire of about 2 mm in outer diameter. It is also possible to stick and fix the light receiving probe 18 to the organism 8, since the same is lightweight and extremely flexible.

FIG. 4 shows the appearance of the embodiment. Referring to FIG. 4, the forward end portion 36 of the light transmission probe 12 and the silicon photodiode 14 of the light receiving probe 18 extending from the apparatus body 46 are stuck and fixed to an organism. The keyboard 28, the liquid crystal display 30, the recorder 32, the alarm device 34 and the like are arranged on the front surface of the apparatus body 46.

Figure 5A:
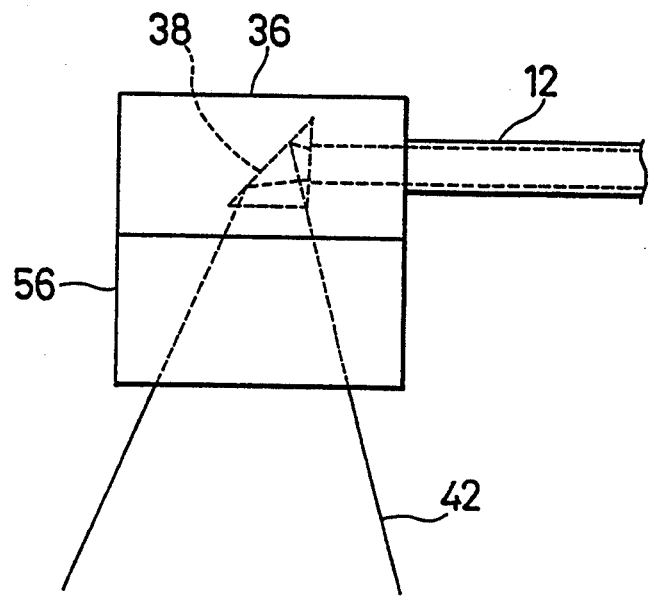
FIG. 5(A) is a side elevational view showing another exemplary light transmission probe.
Figure 5B:
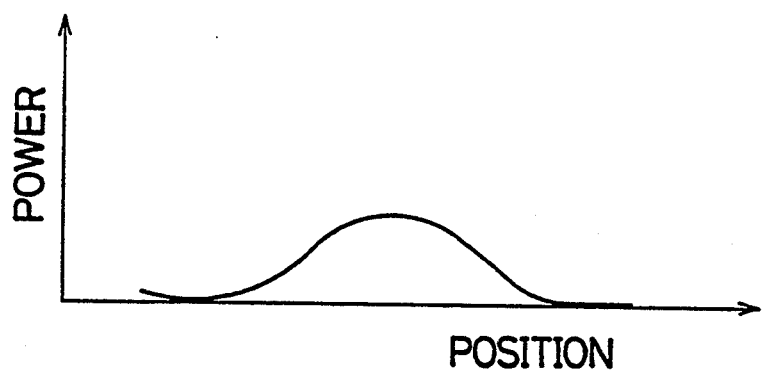
FIG. 5(B) is a graph showing power distribution of laser light as applied.

FIG. 5(A) is a side elevational view showing a forward end portion 36 of another exemplary light transmission probe, and FIG. 5(B) is a graph showing power distribution of laser light as applied.

Referring to FIG. 5(A), a spacer 56 of a light transmitting material is provided in a part of the forward end portion 36 to be in contact with an organism. Due to provision of such a transparent spacer 56, the spot diameter of laser light is inreased on the skin surface to reduce energy density.

Since an organism is a strong scatterer with respect to light, intensity of light reaching a detection side is hardly changed even if slightly spread light is incident upon the organism, while safety is improved since no laser light of high concentration is converged to the organism.

In order to merely increase the spot diameter of the laser light as applied, the forward end portion of the probe may be separated from the exposed portion of the organism, while the transparent spacer 56 is arranged in the separated part to effectively oppress the measured portion of the organism. In order to measure a head portion, for example, the transparent spacer 56 is adapted to oppress the organism to displace blood flow in the skin covering the skull, thereby obtaining information from a deep portion with smaller influence exerted by the blood flow in the exterior of the brain. To this end, the transparent spacer 56 is preferably provided with elasticity. Due to provision of such a transparent spacer 56, it is possible to physically prevent the organism from erroneous approach of high concentration light from the forward ends of the optical fibers.

A detection system generally employed in an optical organism measuring apparatus is adapted to receive light which is transmitted through or reflected by an organism through an optical fiber bundle and to guide the light to a photomultiplier. Sensitivity of such a conventional detection system is now compared with that of the detection system employing a solid state detector according to the present invention. While a photomultiplier is superior in sensitivity to a silicon photodiode in general, it is necessary to receive light from an organism through an optical fiber bundle due to a large element size. On the other hand, the silicon photodiode can be directly fixed to an organism since the same has a small size. In order to compare these detection systems with each other as to sensitivity of the optical organism measuring apparatuses, it is necessary to compare sensitivity levels of th overall detection systems including optical loss values in optical fiber bundles.

(a) Sensitivity of the detection system employing a silicon photodiode is now approximated.

It is assumed that a measuring wavelength is 800 nm and the size of a light receiving surface is 10 mm by 10 mm. Spectral sensitivity of 0.55 A/W is attained with a commercially available silicon photodiode element.

(b) Sensitivity of the detection system employing a photomultiplier is now approximated.

It is assumed that measuring wavelength is 800 nm, and a multialkali photoelectric surface is used. A commercially available photomultiplier has cathode sensitivity of 8.5 mA/W, a current amplification factor of $2 \times 10^4$ with an applied voltage of 600 V, and anode sensitivity of 170 A/W, for example.

Light loss of each optical fiber bundle is calculated. Assuming that the optical fiber bundle has an outer diameter of 2 mm and an optical fiber charging rate of 70%, a core ratio of the optical fiber is 64%, a probability of propagation of transmitted or reflected light incident upon the core is about 20%, and loss which is caused by reflection, transmission and bending at an end surface of the optical fiber, i.e., fiber loss, is 10%, actual sensitivity of the detection system employing the photomultiplier is as follows:

$$(\text{detector sensitivity}) \times (1 - \text{fiber loss})$$

With the aforementioned numerical values, the actual sensitivity is as follows:

$$\begin{aligned}(\text{actual sensitivity}) &= 170 \times 0.7 \times 0.64 \times 0.2 \times (1 - 0.1) \\ &= 13.7 \text{ (A/W)}\end{aligned}$$

When light outgoing from a strong scatterer such as an organism is detected, a light receiving area of the detector is proportionate to the detected quantity of light. While the silicon photodiode can detect the quantity of light received from the portion of 10 mm by 10 mm, the photomultiplier can merely detect light which is received from a portion of 2 mm in diameter. Therefore, area correction is required for comparing sensitivity levels. The sensitivity of the silicon photodiode is virtually $10^2/\pi \times 1^2 = 31.8$ times as compared with that of the photomultiplier. Therefore, corrected sensitivity of the silicon photodiode is $0.55 \times 31.8 = 17.5$ (A/W). Thus, the detection system employing a silicon photodiode is rather superior in sensitivity to that employing a photomultiplier.

Although it is possible to improve the sensitivity of the detection system employing the photomultiplier by increasing the applied voltage or the diameter of the light receiving optical fiber bundle, it is unpreferable to excessively increase the voltage which is applied to the photomultiplier since the signal is detected with presence of disturbance light to some extent in clinical application. When the optical fiber bundle is increased in diameter, further, it is difficult to fix the same to an organism since its own weight is also increased.

Consequently, it may be advantageous to use a solid state detector such as a silicon photodiode as a detector for optical organism measurement in view of sensitivity as well as fixation to an organism particularly in transmission measurement, as compared with a photomultiplier.

According to the aforementioned calculation, such a conclusion has been drawn that the silicon photodiode is advantageous in sensitivity by about 1.3 times as compared with the photomultiplier. In addition, the silicon photodiode is further advantageous in view of the cost with a high practical value since no high-priced optical fiber bundle nor photomultiplier is employed. This particularly contributes to an apparatus which is provided with a plurality of detector portions.

Although three wavelengths are employed in the aforementioned embodiment, four or more wavelengths may alternatively be employed in order to improve measuring accuracy.

Further, the apparatus may comprise only one semiconductor laser, to obtain vital information by measuring absorbance at a specific wavelength.

According to the present invention, a light source is formed by a semiconductor laser to transmit laser light to an organism through a single core optical fiber while the measuring light transmitted through the organism is directly received by a solid state detector of a large area through no optical fiber, whereby it is possible to guide light of a specific wavelength to the organism with high power, for detecting the light transmitted through the organism in high sensitivity.

The probes to be in contact with the organism can be reduced in size and weight in a range applicable in a clinical field, thereby facilitating fixation of the apparatus to the organism.

The light receiving side can be extremely reduced in cost due to employment of the solid state detector. Even if a plurality of detectors are employed for measuring a plurality of portions, for example, it is possible to suppress increase of the cost. The present invention is particularly effective when one light transmission portion is combined with a plurality of light receiving portions.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An optical organism measuring apparatus for applying light of one or more specific wavelengths to an organism and detecting said light being transmitted through or reflected by said organism thereby obtaining vital information, said apparatus comprising:
    a light application means, including:
        a plurality of semiconductor lasers of different wavelengths;
        a plurality of single core optical fibers coupled with said semiconductor lasers, respectively;
        a light application probe means containing light emitting ends of said plurality of said single core optical fibers;
    a light detection means, including a light detection probe means with a solid state detector integrated with a preamplifier for receiving said light from said organism;
    a cable connecting said light application probe means to a light detection circuit;
    a sample-and-hold circuit adapted to sample and hold a signal from said light detection probe means, which is amplified by said preamplifier; and
    a main amplifier adapted to amplify an output signal from said sample-and-hold circuit.

2. An apparatus according to claim 1, wherein said light application probe means is provided with a prism means for changing the direction of said laser light passing through said single core optical fibers perpendicularly prior to being applied to an organism.

3. An apparatus according to claim 1, wherein said plurality of semiconductor lasers are coupled with said plurality of single core optical fibers by laser modules.

4. An apparatus according to claim 2, wherein said plurality of semiconductor lasers are coupled with said plurality of single core optical fibers by laser modules.

5. An apparatus according to claim 1, wherein said plurality of single core optical fibers are bundled into a sheath within said light application probe means.

6. An apparatus according to claim 1, including a cable connecting said light application probe means to a light detection circuit.

7. An apparatus according to claim 6, wherein said cable is made of flexible shielding wire.

8. An apparatus according to claim 1, including a V-F converter means for an amplified signal voltage from said main amplifier to a frequency, and a central processing unit receiving an output signal from said V-F converter.

* * * * *